US011331982B2

(12) United States Patent
Huang et al.

(10) Patent No.: US 11,331,982 B2
(45) Date of Patent: May 17, 2022

(54) PORTABLE APPARATUS AND METHOD OF PURIFYING AIR FOR BREATHING

(71) Applicant: FORD GLOBAL TECHNOLOGIES, LLC, Dearborn, MI (US)

(72) Inventors: Daniel C. Huang, Rochester Hills, MI (US); Kevin Michael Swenskowski, Dearborn Heights, MI (US); John Craig Elson, Farmington Hills, MI (US); Clay Wesley Maranville, Ypsilanti, MI (US); Lawrence C. Karas, New Boston, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 616 days.

(21) Appl. No.: 16/366,473

(22) Filed: Mar. 27, 2019

(65) Prior Publication Data
US 2020/0307359 A1 Oct. 1, 2020

(51) Int. Cl.
*B01D 46/10* (2006.01)
*B01D 46/42* (2006.01)
*B01D 53/04* (2006.01)
*B60H 3/06* (2006.01)
*B60N 2/75* (2018.01)
*A62B 7/10* (2006.01)
*B01D 46/00* (2022.01)

(52) U.S. Cl.
CPC ............... *B60H 3/06* (2013.01); *A62B 7/10* (2013.01); *B01D 46/0027* (2013.01); *B01D 46/10* (2013.01); *B01D 2253/102* (2013.01); *B01D 2256/12* (2013.01); *B01D 2257/93* (2013.01); *B60H 2003/0691* (2013.01)

(58) Field of Classification Search
CPC ........ B01D 46/10; B01D 46/42; B01D 53/04; B60H 1/246; B60H 3/0658; B60N 2/75
USPC .......................... 55/385.3, 471–473, DIG. 34
See application file for complete search history.

(56) References Cited

U.S. PATENT DOCUMENTS

| 5,160,517 A | * | 11/1992 | Hicks | ....................... A61G 5/10 |
| | | | | 55/385.1 |
| 6,773,477 B2 | | 8/2004 | Lindsay | |
| 9,701,172 B2 | * | 7/2017 | Tsuzaki | ................ B60N 2/5635 |
| 2004/0031248 A1 | * | 2/2004 | Lindsay | .................... F24F 8/10 |
| | | | | 55/385.3 |

(Continued)

FOREIGN PATENT DOCUMENTS

| CN | 202192968 U | 4/2012 |
| CN | 202192969 U | 4/2012 |

(Continued)

OTHER PUBLICATIONS

English Machine Translation of CN105059197B dated Mar. 8, 2017.

(Continued)

*Primary Examiner* — Minh Chau T Pham
(74) *Attorney, Agent, or Firm* — Vichit Chea; Price Heneveld LLP

(57) ABSTRACT

An apparatus and method are provided for purifying air for breathing. The apparatus includes an armrest having a receiver and an air purification module releasably received in the receiver. The air purification module is portable and displaceable between a first operating position held in the receiver and a second operating position remote from the armrest and the vehicle.

17 Claims, 9 Drawing Sheets

(56) References Cited

U.S. PATENT DOCUMENTS

| | | | | |
|---|---|---|---|---|
| 2005/0097870 | A1* | 5/2005 | Moshenrose | B01D 53/32 55/385.1 |
| 2005/0229557 | A1* | 10/2005 | Little | A47C 7/383 55/385.1 |
| 2006/0042205 | A1* | 3/2006 | Kalous | F24F 3/163 55/385.1 |
| 2010/0081369 | A1* | 4/2010 | Space | B60N 2/565 454/76 |
| 2018/0154297 | A1* | 6/2018 | Maletich | B01D 46/442 |
| 2018/0326811 | A1* | 11/2018 | Chelian | B60H 1/008 |
| 2021/0331112 | A1* | 10/2021 | Kim | A47L 9/2852 |

FOREIGN PATENT DOCUMENTS

| | | |
|---|---|---|
| CN | 202429028 U | 9/2012 |
| CN | 104015589 A | 9/2014 |
| CN | 203854463 U | 10/2014 |
| CN | 204821048 U | 12/2015 |
| CN | 106183725 A | 12/2016 |
| CN | 105059197 B | 3/2017 |
| CN | 106976377 A | 7/2017 |
| CN | 107097835 A | 8/2017 |
| CN | 207842603 U | 9/2018 |
| GB | 2474496 A | 4/2011 |

OTHER PUBLICATIONS

English Machine Translation of CN204821048U dated Dec. 2, 2015.
English Machine Translation of CN203854463U dated Oct. 1, 2014.
English Machine Translation of CN106976377A dated Jul. 25, 2017.
English Machine Translation of CN207842603U dated Sep. 11, 2018.
"Atmosphere Drive"; Amway; https://www.amway.mylen/Brands/ATMOSPHERE/ATMOSPHERE-DRIVE/p/121637; pp. 1-3; printed on Jan. 23, 2019.
English Machine Translation of CN202429028U dated Sep. 12, 2012.
English Machine Translation of CN202192969U dated Apr. 18, 2012.
English Machine Translation of CN202192968U dated Apr. 18, 2012.
English Machine Translation of CN107097835A dated Aug. 29, 2017.
English Machine Translation of CN106183725A dated Dec. 7, 2016.
English Machine Translation of CN104015589A dated Sep. 3, 2014.

* cited by examiner

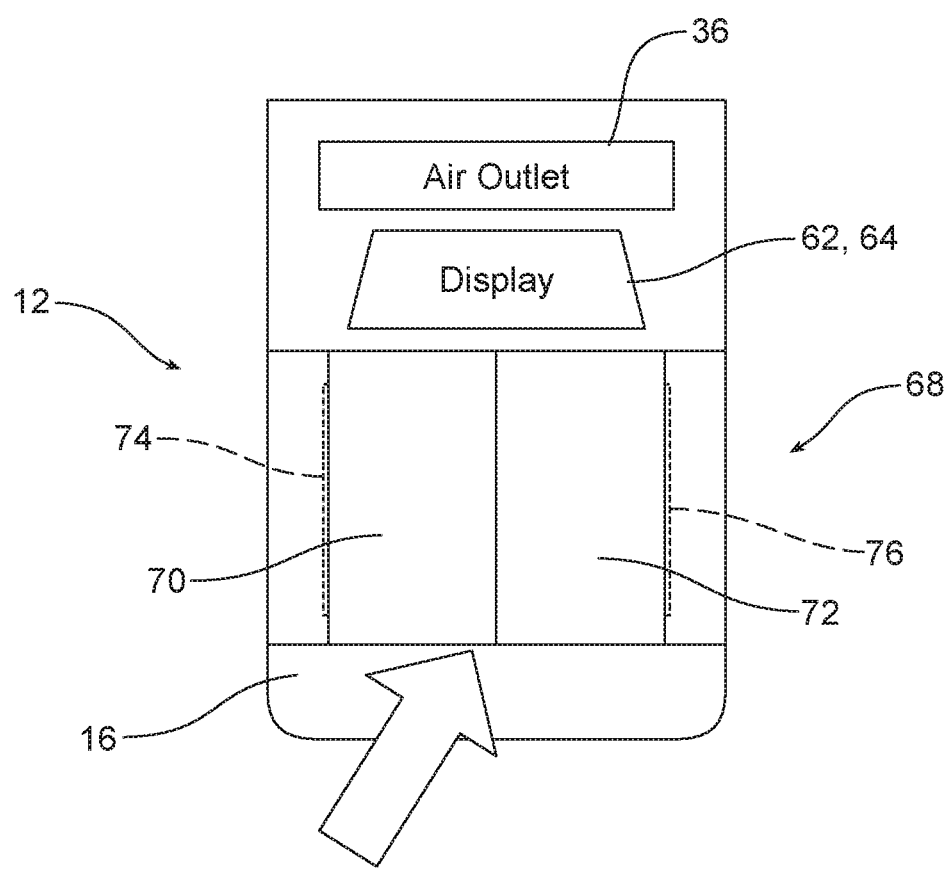

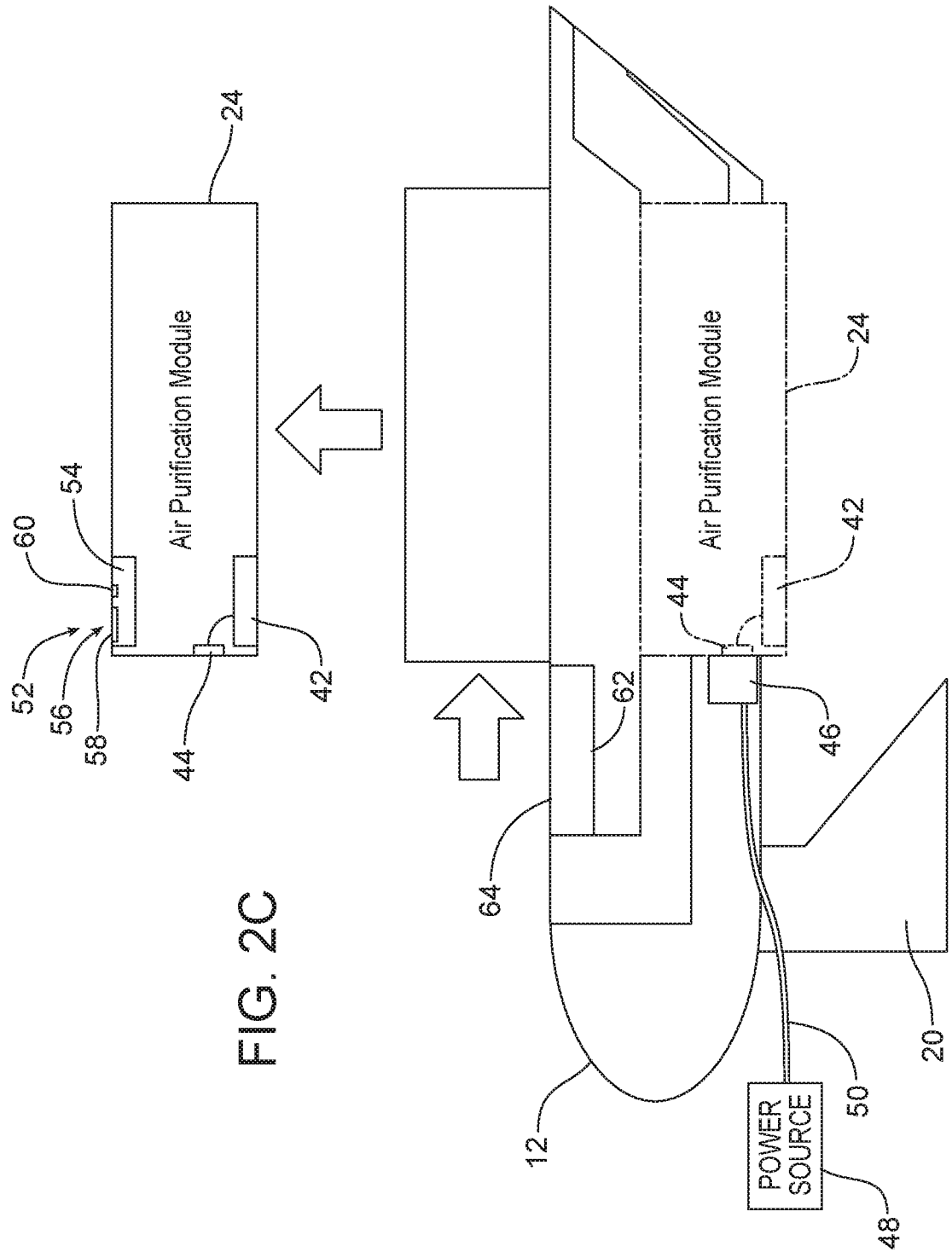

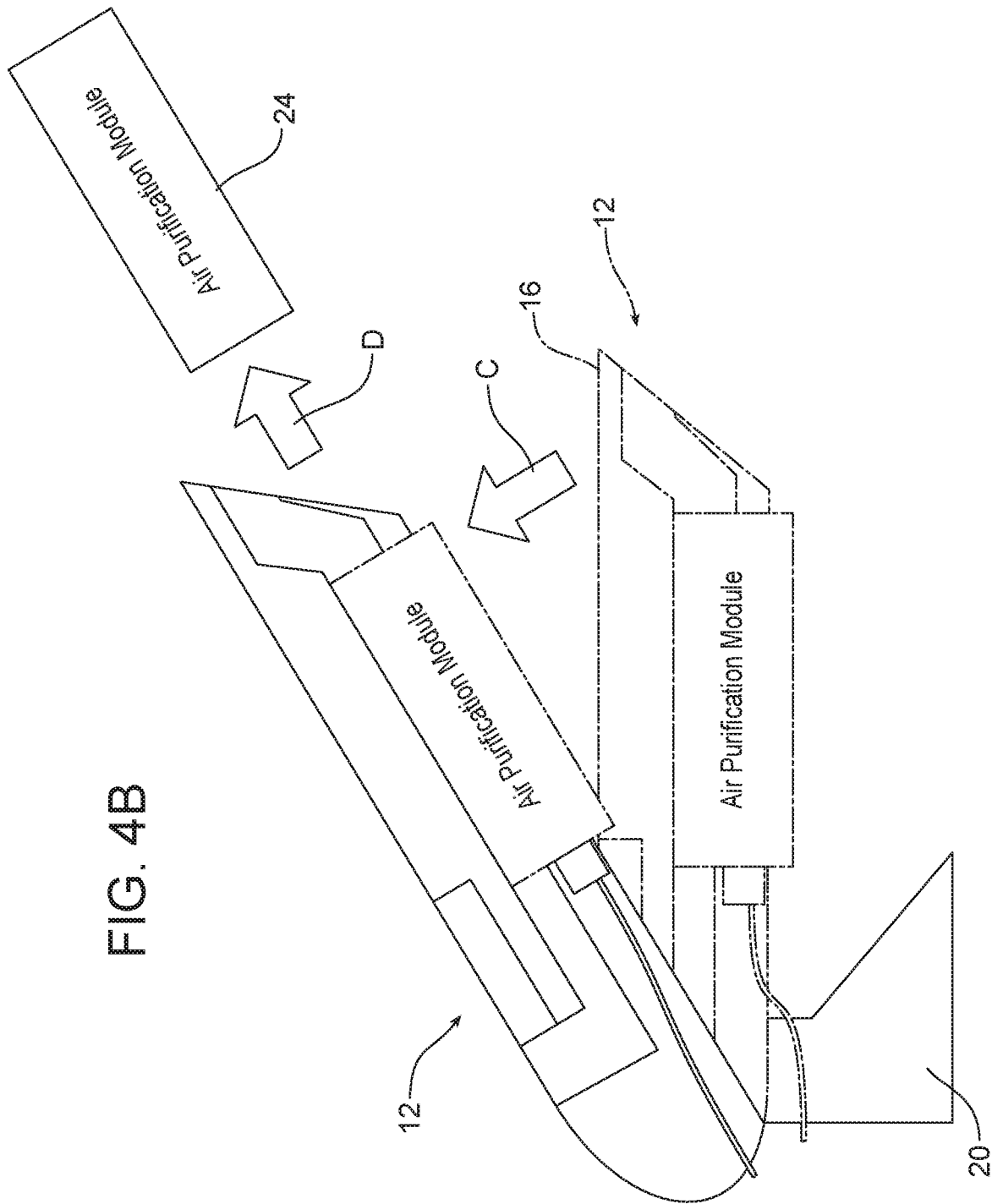

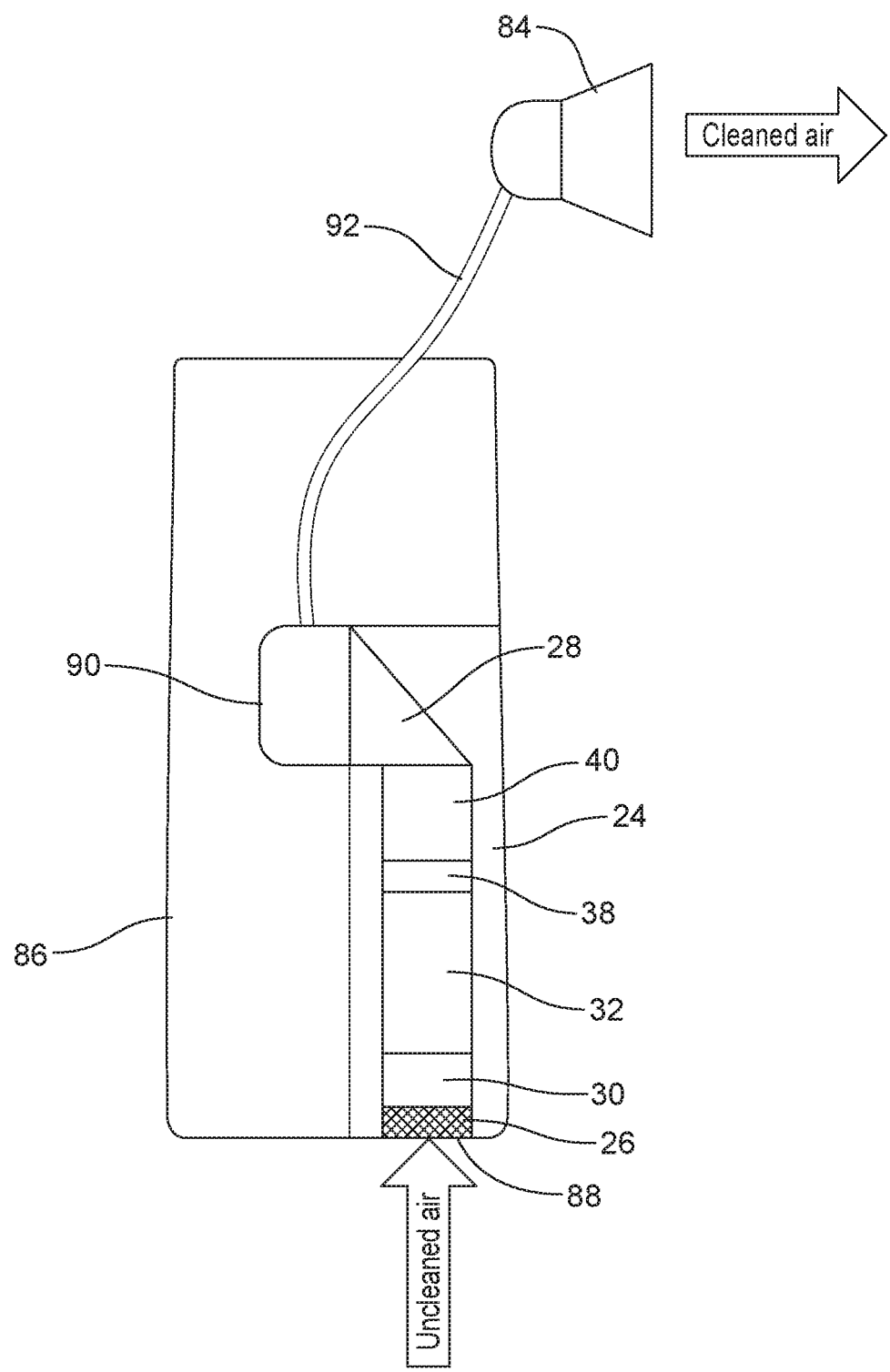

PORTABLE APPARATUS AND METHOD OF PURIFYING AIR FOR BREATHING

TECHNICAL FIELD

This document relates generally to the vehicle equipment field and, more particularly, to a portable apparatus and method adapted for purifying air in the vehicle and at a remote location outside of the vehicle for breathing.

BACKGROUND

This document relates to a new and improved apparatus that is integrated into the armrest of a vehicle and operable in this first position to purify air within the passenger cabin or compartment of the motor vehicle. Advantageously, the apparatus further includes an air purification module that is portable and may be released from the armrest and taken with the user to purify the air remote from or outside the motor vehicle as desired.

SUMMARY

In accordance with the purposes and benefits described herein, a new and improved apparatus is provided comprising an armrest, including a receiver, and an air purification module. The air purification module is releasably received in the receiver and displaceable between a first operating position held in the receiver and a second operating position remote from the armrest. Thus it should be appreciated that the air purification module may be removed from the motor vehicle by the operator and used to purify air for breathing while walking through the ambient environment or at a remote location such as a room or office.

The air purification module may include an air inlet port, a fan, a filter and an air outlet port. The air purification module may include a particulate sensor to detect air quality. The air purification module may include an ionizer to ionize and clean the air passing through the air purification module. The air purification module may further include a rechargeable energy source such as a lithium battery.

The air purification module may include a control module. That control module may include a controller and a human interface of any appropriate type allowing for communication between the operator and the controller. That human interface may include an electronic display and an actuator switch, a touchscreen display, a voice processor for voice command or the like.

The air purification module may include a first set of electrical contacts connected to the rechargeable energy source. The armrest may include a second set of electrical contacts that cooperate with the first set of electrical contacts to charge the rechargeable energy source when the air purification module is in the first operating position held in the receiver in the armrest.

The armrest may include an air inlet and an air outlet. That air inlet communicates with the air inlet port of the air purification module to allow the intake of air from the passenger cabin of the vehicle. The air outlet may communicate with the air outlet port of the air purification module allowing the discharge of purified air back into the passenger cabin of the vehicle.

The armrest may include a body having a pad for comfortably supporting the arm of a vehicle occupant and a hinge connecting the body to a hinge support of a console of the vehicle. This allows the armrest to be tipped up to allow access to any underlying console feature or for any other desired purpose.

In addition, the apparatus may include a releasable latching feature adapted to retain the air purification module in the receiver of the armrest when the air purification module is in the first operating position. In one of many possible embodiments, that receiver may be provided in the body concealed under the pad.

In one possible embodiment of the apparatus, the pad includes an access door which may be opened to access the air purification module and remove the air purification module from the armrest. That access door may include a first door panel and a second door panel carried on opposed pivots.

In accordance with an additional aspect, an apparatus comprises (a) an armrest including a body having a pad and a receiver, (b) an air purification module held in the receiver and operable in a first operating position inside a vehicle and a second operating position remote from or outside the vehicle and (c) a releasable latching feature for releasing the air purification module from the receiver.

The air purification module may include an air inlet port, a fan, a filter and an outlet port. The air purification module may further include a particulate sensor, an ionizer, a rechargeable energy source and a control module of the type described above.

In accordance with yet another aspect, a method is provided of purifying air for breathing. That method comprises the steps of: (a) retaining an air purification module in a receiver of an armrest within a vehicle, (b) operating that air purification module when in the vehicle to purify air in a passenger compartment of the vehicle for breathing, (c) removing the air purification module from the vehicle when leaving the vehicle and (d) operating the air purification module remote from the vehicle to purify air outside of the vehicle for breathing.

In the following description, there are shown and described several preferred embodiments of the apparatus and related method of purifying air for breathing. As it should be realized, the apparatus and method are capable of other, different embodiments and their several details are capable of modification in various, obvious aspects all without departing from the apparatus and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the apparatus and method and together with the description serve to explain certain principles thereof.

FIG. 2A is a schematic top plan view of a first possible embodiment of the apparatus as illustrated in FIG. 1 showing the access door in a closed position concealing the air purification module.

FIG. 2C is a schematic side elevational view illustrating the removal of the air purification module from the receiver in the armrest to allow the air purification module to be transported to a second operating position at any desired location remote from the armrest and the vehicle.

Figure 3A:
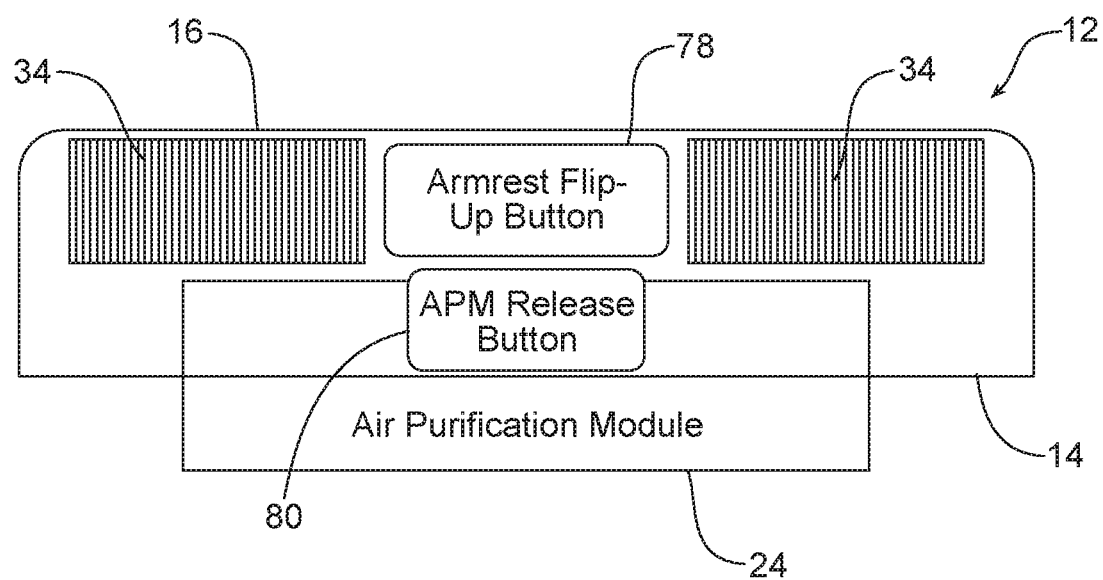
Figure 3B:
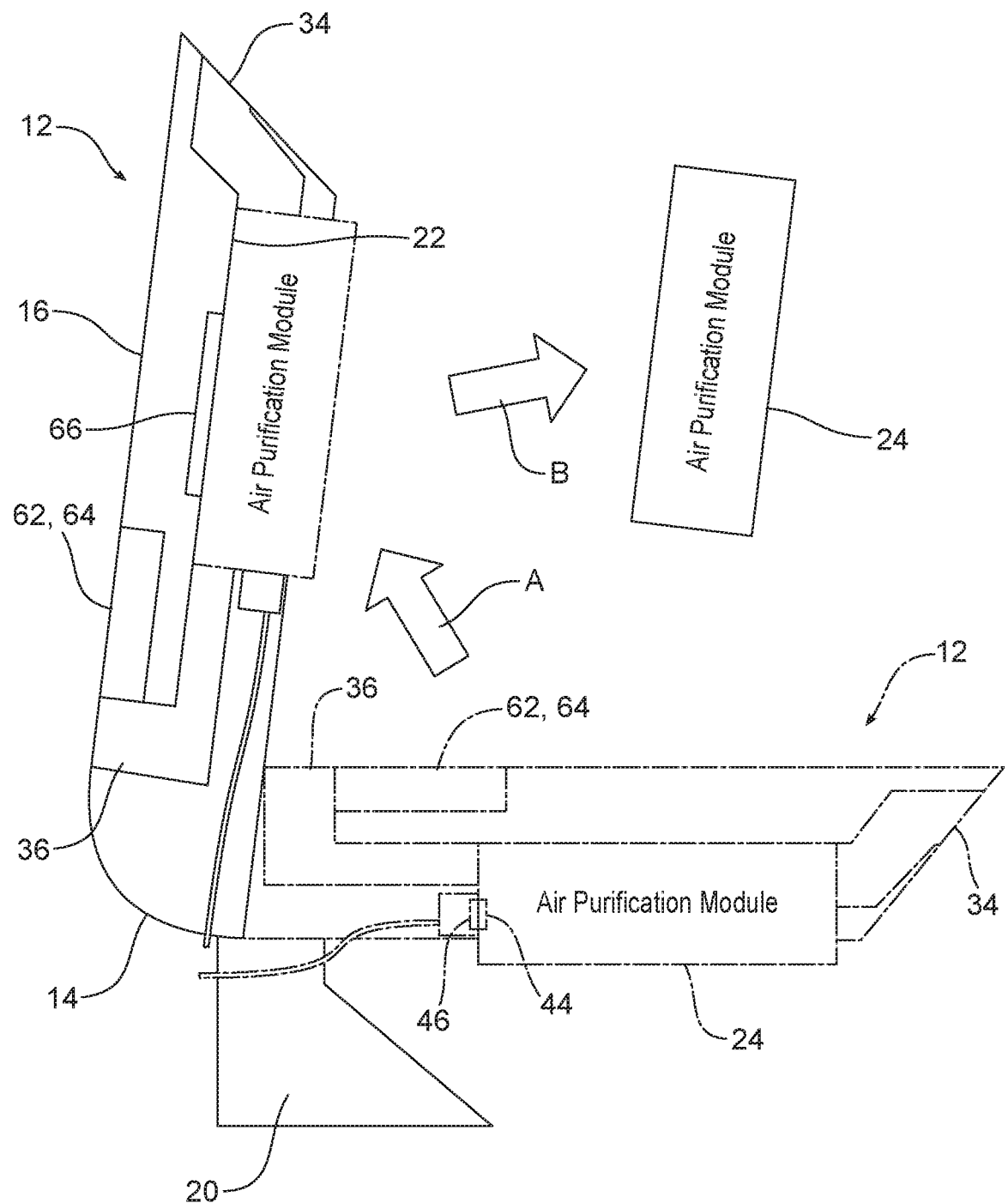

FIGS. 3A and 3B are schematic illustrations of a second possible embodiment of the apparatus wherein the air purification module is removed from the receiver of the armrest by tilting the armrest upward and then withdrawing the air purification module from the receiver. More particularly, FIG. 3A is a front elevational view illustrating the actuators utilized to complete the removal of the air purification module from the armrest. FIG. 3B is a schematic side elevational view illustrating the two-step removal process.

Figure 4A:
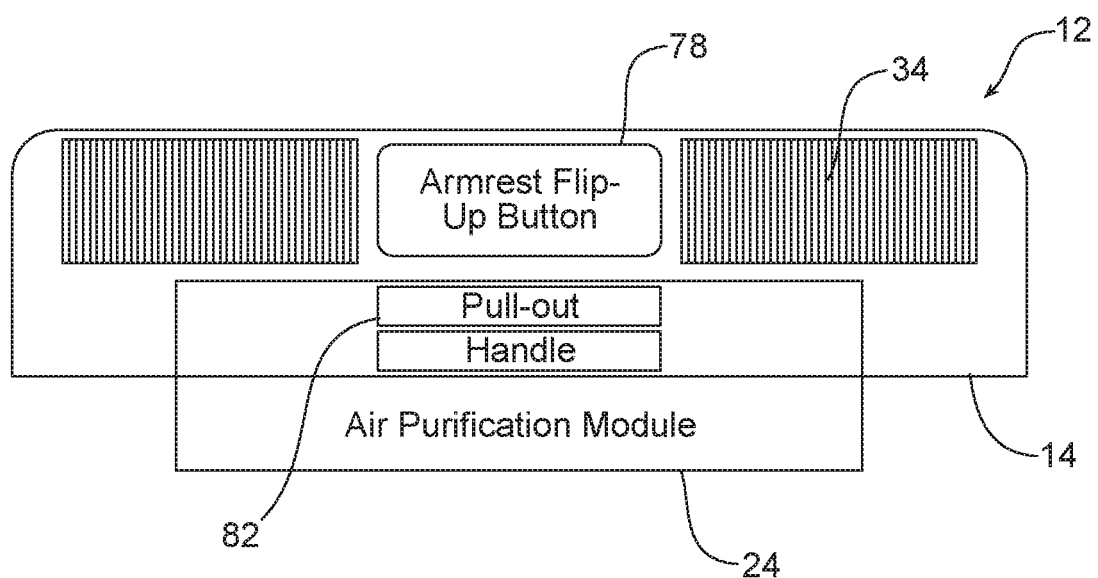

FIGS. 4A and 4B illustrate yet another possible alternative embodiment of the apparatus wherein the air purification module is removed from the armrest by sliding forward out of the front end of the armrest. More particularly, FIG. 4A illustrates a front elevational view of the armrest while FIG. 4B is a schematic side elevational view illustrating a two-step process for removing the air purification module from the receiver in the armrest.

FIG. 5 is a schematic illustration showing the portable air purification module removed from the armrest and in operation remote from the vehicle. An optional breathing mask is shown connected to the air purification module.

Reference will now be made in detail to the present preferred embodiments of the apparatus and method, examples of which are illustrated in the accompanying drawing figures.

DETAILED DESCRIPTION

Figure 1:
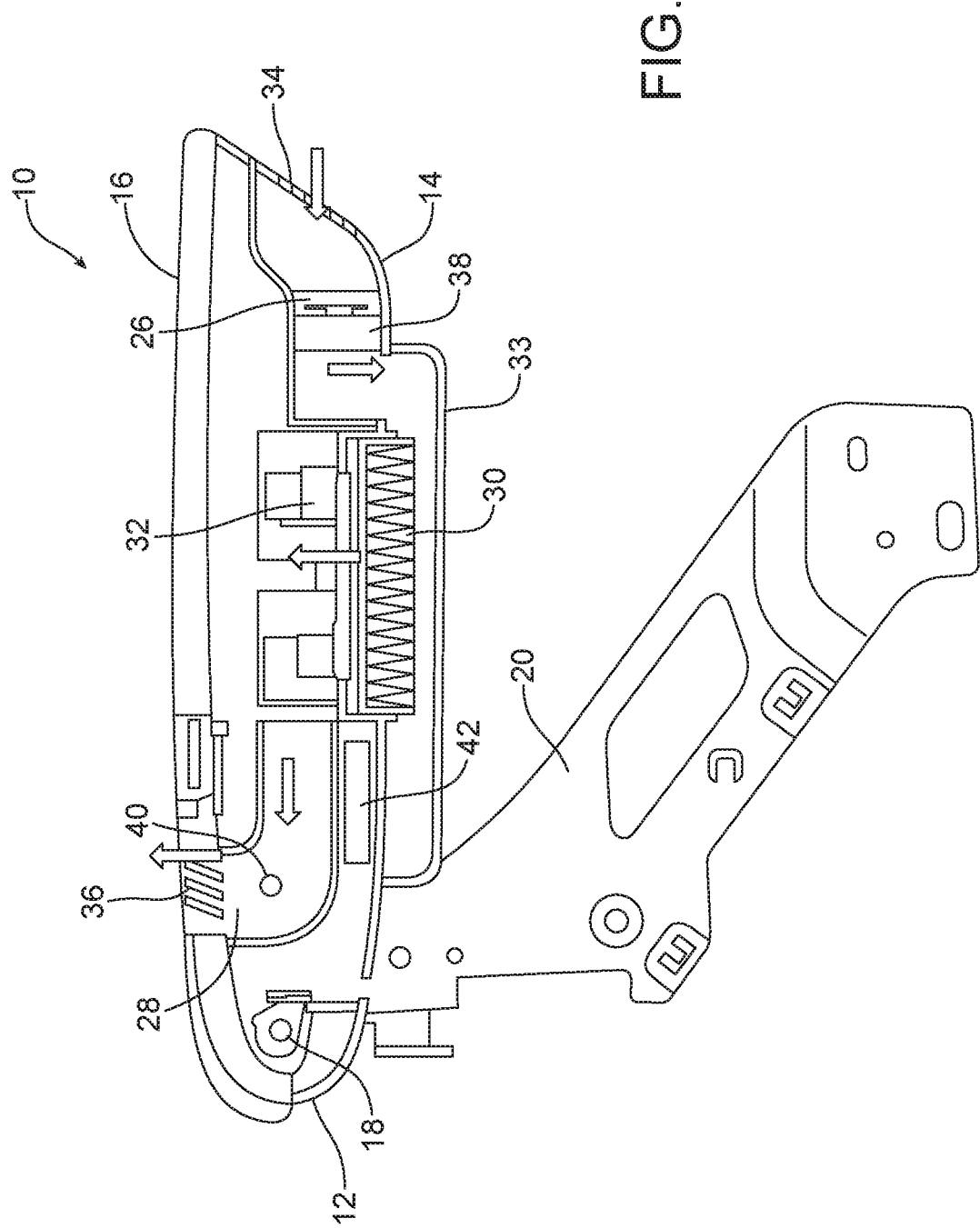
FIG. 1 is a schematic illustration of one possible embodiment of the new and improved apparatus for purifying air for breathing wherein the air purification module of that apparatus is illustrated in a first operating position held in a receiver of an armrest.

Reference is now made to FIG. 1 which schematically illustrates a first possible embodiment of the apparatus 10 for purifying air for breathing. The apparatus 10 includes an armrest 12. The armrest 12 includes a body 14 having a pad 16 overlying the top surface thereof and adapted for cushioning an arm of an occupant of the motor vehicle. A hinge 18 connects the body 14 to a hinge support 20 that may be connected to a console (not shown) of the vehicle in which the armrest is mounted.

As should be further appreciated from reviewing FIGS. 1, and 2A-2C, the armrest 12 further includes a receiver 22 that is sized and shaped to receive and hold an air purification module 24. As will become apparent from the following description, the air purification module 24 is releasably received in the receiver 22 and displaceable between a first operating position held in the receiver (see FIGS. 1 and 2A) and a second operating position remote from the armrest 12 (see FIG. 2C). Thus, it should be appreciated that the air purification module 24 is portable and may be used to purify air at substantially any place and at any time desired by the operator.

More particularly, the air purification module 24 includes an air inlet port 26, an air outlet port 28, a filter 30 between the air inlet port and the air outlet port and a fan 32. The fan 32 is adapted to draw air in through the air inlet port 26 and the filter 30, where that air is purified, and then push that air through the air outlet port 28 where the purified air is returned to the environment.

In the embodiment illustrated in FIGS. 1 and 2A-2C, it should be appreciated that the armrest 12 includes an air inlet 34 and an air outlet 36 wherein the air inlet is in fluid communication with the air inlet port 26 and the air outlet is in fluid communication with the air outlet port 28 when the air purification module 24 is in the first operating position held in the receiver 22.

The filter 30 may be a replaceable filter of any appropriate construction including, for example, a HEPA filter, a MERV filter, an activated carbon filter, a permanganate filter or even any combination of these. Such a filter 30 may assume the form of a replaceable cartridge if desired. Such a cartridge may be easily replaced by removing a filter cover 33.

The air purification module 24 may also incorporate any of a number of additional structures including, for example, the particulate sensor 38 for measuring or ascertaining the quality of the air flowing through the air purification module 24. That sensor may comprise any type of sensor known in the art to be suitable for this purpose including, for example, a PM sensor (i.e. 2.5, 1) a laser sensor, an optical sensor or the like. That air purification module 24 may also include an ionizer 40 for ionizing the air drawn through the air purification module 24 by the fan 32. In the illustrated embodiment, the ionizer 40 is downstream from the filter 30. Note action arrows illustrating the flow of air through the air purification module 24.

The air purification module 24 also includes a rechargeable energy source 42 of a type known in the art including a battery such as a lithium ion battery, a fuel cell or other power source appropriate for powering the air purification module 24. As illustrated in FIG. 2C, the air purification module 24 may include a first set of electrical contacts 44 connected to the rechargeable energy source 42 while the armrest 12 includes a second set of electrical contacts 46. When the air purification module 24 is in the first operating position in the receiver 22 of the armrest 12, the first and second set of electrical contacts 44, 46 are engaged thereby allowing recharging of the rechargeable energy source 42 by a connection with a power source 48 of the motor vehicle through the wiring harness 50. See phantom line showing in FIG. 2C. In one particularly useful embodiment of the apparatus 10, the second set of electrical contacts 46 are incorporated into a charging shoe of a type known in the art and adapted for docking with the portable air purification module 24.

The air purification module 24 may also include a control module 52 for monitoring and operating the air purification module 24. In one possible embodiment, the control module 52 includes a controller 54 in the form of a dedicated microprocessor or electronic control unit (ECU) operating in accordance with instructions from appropriate control software. Such a controller 54 may include one or more processors, one or more memories and one or more network interfaces all in communication with each other over one or more communication buses. The control module 52 may also include a human interface 56. That human interface 56 may include an electronic display 58 and an actuator switch 60. In alternative embodiments, the human interface 56 and electronic display 58 and the actuator switch 60 may all be merged into a touchscreen display.

In any of the possible embodiments, the control module 52 may include a voice processor to allow for voice command and control of the operation of the air purification module 24. Further, the control module 52 may also be configured for remote wireless operation allowing an operator to access real-time air quality information and control of the air purification module 24 via cell phone through an appropriate cell phone app. Such communication could be based upon Bluetooth wireless technology.

Here it should also be noted that the control of the operation of the air purification module 24 may not necessarily be limited to the control module 52 carried on the air purification module 24. When the air purification module 24 is docked or held in the receiver 22 of the armrest 12, the control module 52 may be synched with the in-car human machine interface (HMI) provided on the center stack (not shown) of the vehicle to display and control the air purification module 24. Alternatively, or in addition, a control module 62 for operating the air purification module 24 may be provided on the upper face of the armrest 12. Note particularly the touchscreen display 64 of control module 62 illustrated in FIGS. 2A-2C.

Figure 2B:
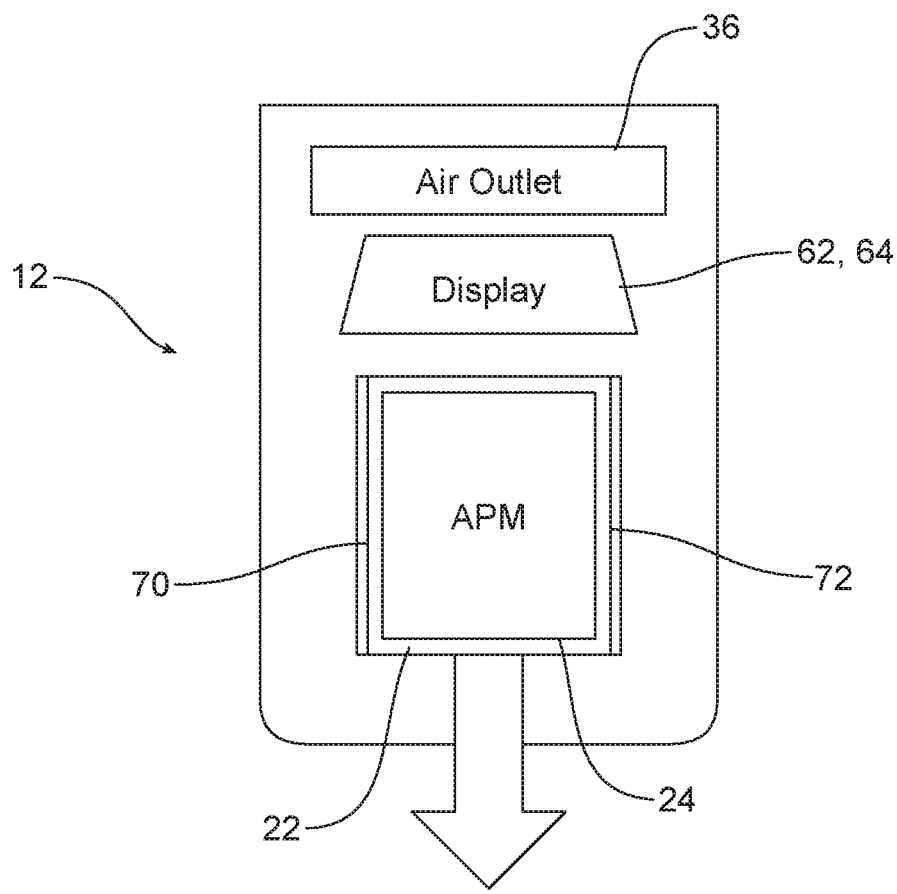
FIG. 2B is a top plan view similar to FIG. 2A but illustrating the access door and, more particularly, the two panels of the access door in the open position.

In the embodiment illustrated in FIGS. 1 and 2A-2C, the receiver 22 is provided in the body 14 concealed under the pad 16. The pad 16 includes an access door, generally designated by reference numeral 68 which may be opened to access the air purification module 24 and remove the air purification module 24 from the receiver 22 in the armrest 12. As best shown in FIG. 2B, the access door 68 in the illustrated embodiment includes a first door panel 70, and a second door panel 72, carried on opposed hinges or pivots 74, 76. The access door 68 may be opened by depressing a switch such as may be found on the touchscreen display 62. When the doors are opened as illustrated in FIGS. 2B and 2C, the user may access the air purification module 24 in order to remove the air purification module 24 from the receiver 22. More particularly, an easily accessed handle (not shown) may be provided on the air purification module 24 to allow one to engage the handle and lift the air purification module upward as illustrated by action arrow in FIG. 2C. The released air purification module 24 may then be transported by the user to substantially any location remote from the vehicle where the air purification module 24 may be operated relying upon energy stored in the rechargeable energy source 42.

An alternative embodiment of the apparatus 10 is illustrated in FIGS. 3A and 3B. In this embodiment, an operator depresses the Armrest Flip-Up Button 78 to displace the armrest 12 from the horizontal position illustrated in phantom line in FIG. 3B to the raised position illustrated in full line in FIG. 3B (note action arrow A). Next the operator pushes the APM Release Button 80 to release the releasable latching feature 66 and remove the air purification module 24 from the armrest 12 (note action arrow B). Once again, the air purification module 24 may then be transported to any desired location by the user and operated using power from the rechargeable energy source 42.

The releasable latching feature 66 functions to hold or retain the air purification module 24 in the receiver 22 of the armrest 12 in the first operating position. The releasable latching feature 66 may be of a type known in the art to be useful for this purpose including, for example, a spring-loaded latch, spring detents or the like.

In the embodiment illustrated in FIGS. 4A and 4B, one slides the air purification module 24 in and out through the front of the armrest 12. Toward this end one first depresses the Armrest Flip-Up Button 78 (see FIG. 4A) and then displaces the armrest 12 from the horizontal position illustrated in phantom line to the raised position illustrated in full line in FIG. 4B (note action arrow C). One then engages the pullout handle 82 to withdraw the air purification module 24 upward in the direction of action arrow D pulling it through the front end of the armrest 12. The released air purification module 24 may then be utilized in a second operating position at any location remote form the armrest 12 using power provided by the rechargeable energy source 42.

Any of the illustrated embodiments described above are useful in a method of purifying air for breathing. That method includes the steps of: retaining the air purification module 24 in the receiver 22 of an armrest 12 within a vehicle, operating the air purification module 24 when in the vehicle to purify air in a passenger compartment of the vehicle for breathing, removing the air purification module 24 from the vehicle when leaving the vehicle and operating the air purification module 24 remote from the vehicle to purify air outside of the vehicle for breathing.

As illustrated in FIG. 5, the air purification module 24 may also be utilized with a personal breathing device such as the illustrated mask 84. In other embodiments, the personal breathing device could be a cannula. As illustrated in FIG. 5 the air purification module 24 is held in a carrying bag or backpack 86. The bottom of the backpack 86 includes an air inlet 88 made of mesh. The fan 32 of the air purification module 24 draws air through the air inlet 88 in the bag or backpack 86 and the air inlet port 26 and the filter 30 of the air purification module. The fan 32 then pushes that air through the ionizer 40. The air is then discharged through the air outlet port 28 of the air purification module 24 into the air receiver 90 which is connected to the breathing mask 84 by the air line 92. The air receiver 90 may be adapted to snap onto the air purification module 24 overlying the air outlet port 28 in a manner known in the art. Advantageously, the configuration illustrated in FIG. 5 allows one to utilize the air purification module 24 when walking from location to location, such as from the vehicle to a building, where air pollution levels make such action desirable.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:
1. An apparatus, comprising:
an armrest including a receiver; and
an air purification module releasably received in said receiver and displaceable between a first operating position held in said receiver and a second operating position remote from said armrest, wherein said air purification module includes a rechargeable energy source and a first set of electrical contacts connected to said rechargeable energy source, and wherein said armrest includes a second set of electrical contacts engaged with said first set of electrical contacts to charge said rechargeable energy source when said air purification module is in said first operating position.
2. The apparatus of claim 1, wherein said air purification module includes an air inlet port, a fan, a filter and an air outlet port.
3. The apparatus of claim 2, wherein said air purification module further includes a particulate sensor.
4. The apparatus of claim 3, wherein said air purification module further includes an ionizer.
5. The apparatus of claim 1, wherein said air purification module includes a control module.
6. The apparatus of claim 5, wherein said control module includes a controller and a human interface.
7. The apparatus of claim 6, wherein said human interface includes an electronic display and an actuator switch.
8. The apparatus of claim 1, wherein said armrest includes an air inlet and an air outlet wherein said air inlet communicates with said air inlet port and said air outlet commu- nicates with said air outlet port when said air purification module is in said first operating position.

9. The apparatus of claim 8, wherein said armrest includes a body having a pad and a hinge connecting said body to a hinge support of a console of a vehicle.

10. The apparatus of claim 9, further including a releasable latching feature retaining said air purification module in said receiver of said armrest.

11. The apparatus of claim 10, wherein said receiver is provided in said body concealed under said pad.

12. The apparatus of claim 11, wherein said pad includes an access door which may be opened to access said air purification module and remove said air purification module from said armrest.

13. The apparatus of claim 12, wherein said access door includes a first door panel and a second door panel carried on opposed pivots.

14. An apparatus, comprising:
an armrest including a body having a pad and a receiver;
an air purification module held in said receiver and operable in a first operating position inside a vehicle and a second operating position remote from said vehicle, wherein said air purification module includes a rechargeable energy source and a first set of electrical contacts connected to said rechargeable energy source, and wherein said armrest includes a second set of electrical contacts engaged with said first set of electrical contacts to charge said rechargeable energy source when said air purification module is in said first operating position; and
a releasable latching feature for releasing said air purification module from said receiver.

15. The apparatus of claim 14, wherein said air purification module includes an air inlet port, a fan, a filter and an air outlet port.

16. The apparatus of claim 15, wherein said air purification module further includes a particulate sensor, an ionizer, and a control module.

17. A method of purifying air for breathing, comprising:
retaining an air purification module in a receiver of an armrest within a vehicle, wherein said air purification module includes a rechargeable energy source and a first set of electrical contacts connected to said rechargeable energy source, and wherein said armrest includes a second set of electrical contacts engaged with said first set of electrical contacts to charge said rechargeable energy source when said air purification module is in said first operating position;
operating said air purification module when in said vehicle to purify air in a passenger compartment of said vehicle for breathing;
removing said air purification module from said vehicle when leaving said vehicle; and
operating said air purification module remote from said vehicle to purify air outside of the vehicle for breathing.

\* \* \* \* \*